United States Patent
Mahr

[11] Patent Number: 5,462,434
[45] Date of Patent: Oct. 31, 1995

[54] DENTAL HAND TOOL CLEARING SHIELD

[75] Inventor: Michael J. Mahr, Bedford, N.Y.

[73] Assignee: Henry Schein, Inc., Port Washington, N.Y.

[21] Appl. No.: 132,378

[22] Filed: Oct. 6, 1993

[51] Int. Cl.⁶ .......................... A61C 17/06; A61C 17/14; A61C 1/16
[52] U.S. Cl. ............................. 433/97; 433/91; 433/116
[58] Field of Search .................... 423/91, 96, 97, 423/116; 134/84, 85, 92, 104.2, 175, 177, 200; 220/213, 252; 4/262, 263, 267

[56] References Cited

U.S. PATENT DOCUMENTS

| | | | |
|---|---|---|---|
| 643,939 | 2/1900 | Deane | 220/213 X |
| 937,519 | 10/1909 | Green | 4/267 |
| 1,257,250 | 2/1918 | Koch | 4/262 |
| 1,799,525 | 4/1931 | Morgan | 134/177 |
| 2,489,967 | 11/1949 | Lavine | 4/263 |
| 2,601,364 | 6/1952 | Byrnes | 134/151 |
| 2,862,519 | 12/1958 | Motis | 4/263 |
| 3,625,231 | 12/1971 | Littrell, Jr. | 134/102 |
| 3,707,042 | 12/1972 | Talaga | 32/27 |
| 3,811,408 | 5/1974 | Thompson | 118/73 |
| 3,918,987 | 11/1975 | Kopfer | 134/95 |
| 3,955,284 | 5/1976 | Balson | 32/27 |
| 3,968,898 | 7/1976 | Beer | 220/213 X |
| 4,137,929 | 2/1979 | Grossman | 134/182 |
| 4,433,698 | 2/1984 | Blaul | 134/56 R |
| 4,623,186 | 11/1986 | Chavarria et al. | 134/175 X |
| 4,768,534 | 9/1988 | Anderson | 134/175 |
| 4,872,837 | 10/1989 | Issalene et al. | 433/91 X |
| 4,949,738 | 8/1990 | Hubbard | 134/104.3 |
| 4,988,485 | 1/1991 | Bene | 422/292 |
| 5,022,858 | 6/1991 | Castellini . | |
| 5,090,433 | 2/1992 | Kamaga | 134/200 |
| 5,122,153 | 6/1992 | Harrel | 433/91 X |
| 5,263,860 | 11/1993 | Shen et al. | 433/91 |

*Primary Examiner*—Nicholas D. Lucchesi
*Attorney, Agent, or Firm*—Rosen, Dainow & Jacobs

[57] ABSTRACT

The invention disclosed herein provides a shield for use in operating dental hand tools outside of a patient's mouth while preventing escape of any matter ejected from the hand tool into the surrounding vicinity, thereby eliminating or substantially reducing the risk that the ejected matter may otherwise contaminate nearby people or equipment. The shield has an enclosure within which the end of a dental hand tool is placed and operated. The shield is removably coupled to a waste line or the like typically already present in a dental office, such as a high volume suction line, a saliva ejector suction line or a cuspidor. The shield contains therein any matter ejected from the hand tool during operation thereof, and such matter is carried away by the waste line. When the enclosure is coupled to the waste line, escape of the matter ejected from the end of the hand tool is substantially prevented except through the waste line. The shield is preferably disposable.

25 Claims, 5 Drawing Sheets

DENTAL HAND TOOL CLEARING SHIELD

BACKGROUND OF THE INVENTION

The invention disclosed herein relates to shields for use in clearing, cleaning, maintaining, etc. dental hand tools (e.g., handpieces and syringes) prior to sterilization or disposal thereof while preventing escape of any matter ejected from the hand tool into the surrounding area where it can otherwise contaminate the person and clothing of individuals, equipment, etc. Such a shield directs the ejected matter into a means which transports the ejected matter away for suitable disposal. The shields are suited for use in a typical dental office where the transporting means may be a suction line (a high volume line, a saliva ejector line or both), or a cuspidor.

Frequently an unsterilized, used dental hand tool is operated outside a patient's mouth to clear, clean or maintain it. While the used hand tool is being openly operated, there is the risk that liquid or solid material on or in the hand tool will separate from the hand tool and contaminate individuals or objects in the surrounding area. The dental hand tools now in common use include high and low speed handpieces, which are driven by pressurized air and may direct pressurized water to the hand tool tip, and three way syringes. In operation those hand tools eject a spray, which, if the hand tool is openly operated pose a contamination risk to the person and clothing of individuals, and objects such as dental equipment in the surrounding area which may later be touched or used while thought to be sterile. In the case of dental handpieces which are driven by pressurized air, they typically generate an aerosol, particularly the high speed handpieces, which may be carried away from the immediate area of the handpiece, to significantly increase the contamination risk. Recently, the spread of highly contagious diseases like AIDS has made open operation of such unsterilized and used hand tools a matter of concern.

The invention addresses that concern by providing a device which substantially prevents the escape of matter from a dental hand tool which is being operated outside a patient's mouth, for example, when cleaning, clearing or maintaining it.

OBJECTS AND SUMMARY OF THE INVENTION

It is an object of the invention disclosed herein to minimize the risk of contamination of persons, clothing, equipment, etc. when operating used and unsterilized dental hand tools outside a patient's mouth.

It is another object of the invention minimize the risk of such contamination in a typical dental office in an inexpensive and simple manner.

It is another object of the invention to minimize the risk of such contamination in a typical dental office by providing an inexpensive, preferably disposable, attachment for equipment already present in the dental office.

It is another object of the invention to provide such an attachment for the high volume suction line, the saliva ejector line and/or the cuspidor typically found in dental offices.

The invention achieves various of the above objects by providing a shield which has an enclosure for the end of a hand tool in which the hand tool may be operated while the shield contains therein any matter ejected from the hand tool during operation thereof, and means for communicating the enclosure with a means for transporting fluidized matter such that matter ejected from the end of the hand tool in the shield is transported away from the shield through the transporting means. When the enclosure is coupled to the transporting means escape of the matter ejected from the end of the hand tool is substantially prevented except through the communicating means into the transporting means.

The transporting means is preferably a waste line already present in a dental office, such as a high volume suction line, a saliva ejector suction line, or a cuspidor, and in accordance with the preferred embodiments of the invention, the shields are configured to be communicated with such suction lines and a cuspidor.

A shield according to the invention comprises an enclosure sized to receive therein an end of the hand tool which is to cleaned, cleared, maintained, etc. from which matter may be ejected during operation of the hand tool. The enclosure has a first opening through which the end of the hand tool may be inserted into and removed from the enclosure. The shield also includes means communicating the enclosure in a substantially fluid-tight manner to a means for transporting fluidized matter such that matter ejected from the end of the hand tool is transported away from the shield through the transporting means. The enclosure when coupled to the transporting means substantially prevents escape of the matter ejected from the end of the hand tool except through the communicating means into the transporting means. "Substantially fluid-tight" and "substantially fluid-tight manner" are meant in the context that all or almost all of the matter ejected from a hand tool operated within the shield is prevented from escaping from the shield, except into the transporting means.

In the illustrated embodiments, the shield comprises means for substantially closing the first opening while the end of the hand tool is within the enclosure. In the preferred embodiments, the closing means comprises a door and means pivotally connecting the door to the shield adjacent the first opening for pivoting between an open position permitting entry of the end of the hand tool into the enclosure and a closed position substantially closing the first opening while the end of the hand tool is within the enclosure. The door connecting means pivotally connects the door to the enclosure such that the door pivots inwardly into the enclosure into its open position and pivots outwardly to its closed position. The door connecting means also pivotally connects the door to the enclosure such that the door pivots outwardly to the outside of the enclosure from its closed position to also selectively open the first opening to permit the end of the hand tool to be removed from the enclosure. Means are preferably provided for releasably engaging the door and holding it in its closed position.

In the preferred embodiments, the first opening has a first portion closed by the door and a second portion adjacent the first portion sized to receive a barrel of the hand tool therein when the door is closed.

In embodiments in which the shield is communicated with a suction line, the communicating means includes an elongated portion which has a second opening and which is configured to be coupled substantially fluid-tight to the suction line with the second opening in communication with the interior of the suction line, whereby the enclosure is in communication with the interior of the suction line in a substantially fluid-tight manner. In the disclosed embodiments, the suction line is tubular, and a valve assembly coupled to the suction line is tubular, and the elongated portion is also tubular and is sized to be friction fitted in a substantially fluid tight manner into the valve assembly. The suction line and valve assembly may be those of a dental office high volume suction line or saliva ejector suction line.

In the preferred embodiments of shields coupled to a suction line, the enclosure is generally tubular and coaxial with the tubular portion, and has a larger diameter than the diameter of the tubular portion, and the communicating means includes a frustro-conical portion connecting the tubular enclosure and the tubular portion.

In another embodiment the shield is coupled to a dental office cuspidor, and the communicating means comprises a sizing of the enclosure adjacent an open end thereof to be received within the cuspidor in a substantially fluid tight manner. In this embodiment, the enclosure preferably is generally of hollow semi-spherical or paraboloidal shape, and the open end has a diameter which is less than the diameter of the open end of the cuspidor, whereby the enclosure may be supported by the cuspidor with the open end of the enclosure in the cuspidor.

BRIEF DESCRIPTION OF THE DRAWINGS

The invention is illustrated in the figures of the accompanying drawings which are meant to be exemplary and not limiting, in which like numerals refer to like or corresponding parts, and in which.

DESCRIPTION OF THE PREFERRED EMBODIMENTS

Figure 1:
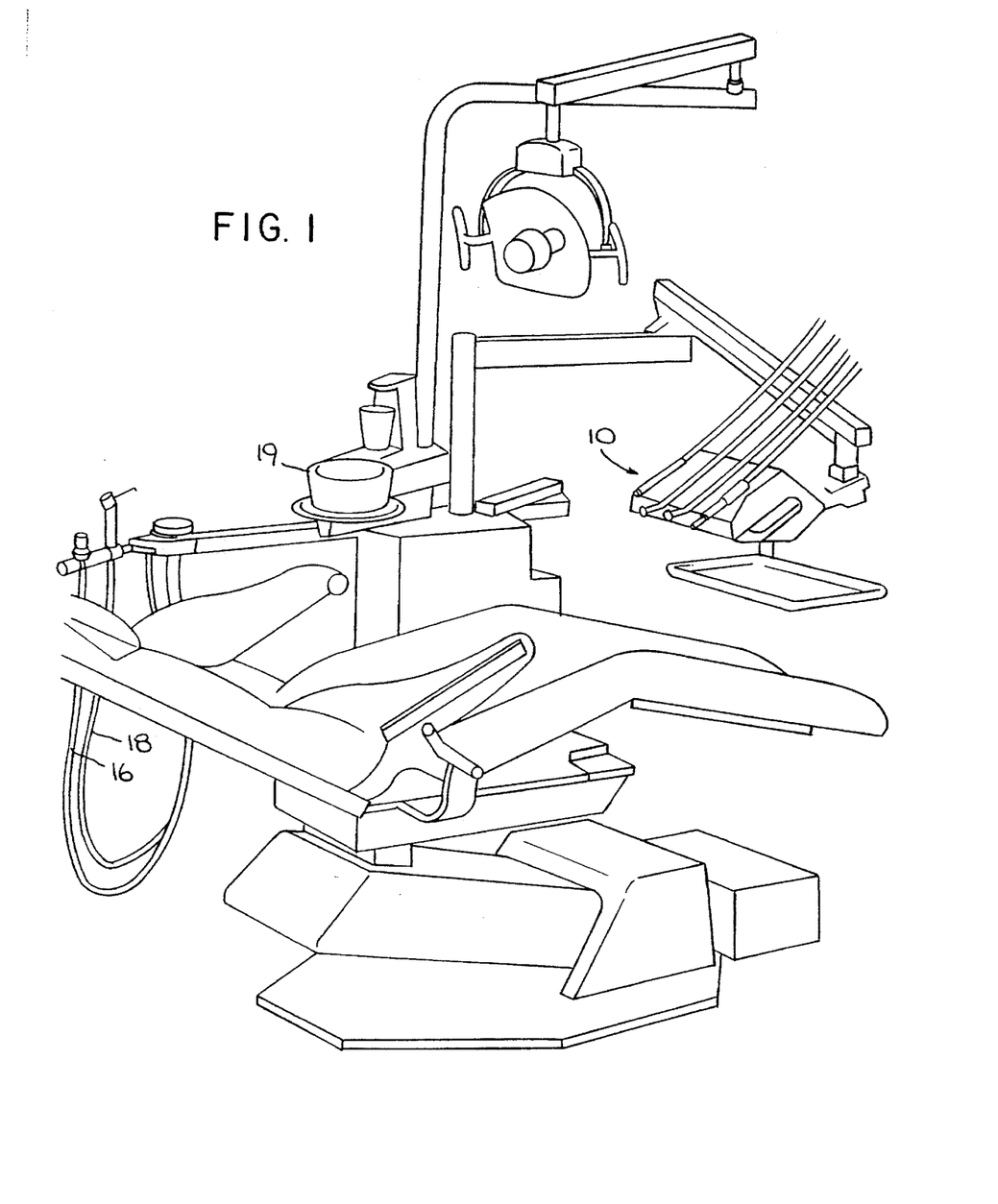
FIG. 1 is a perspective view of a dental office patient's chair and dental equipment including hand tools, cuspidor, suction lines, etc., associated with the chair in a typical dental office.

The drawings illustrate three embodiments of shields according to the invention for use with a dental office high volume suction line (FIGS. 2–8), a dental office saliva ejector line (FIGS. 9–11) and a dental office cuspidor (FIGS. 12–14) which are present in a typical dental office depicted in FIG. 1. Referring to FIG. 1, a typical dental office includes in addition to the chair and light fixture a series of hand tools referenced generally by 10 including high and low speed dental handpieces and a three way syringe, and a high volume suction line 16, a saliva ejector line 18 and a cuspidor 19.

Figure 2:
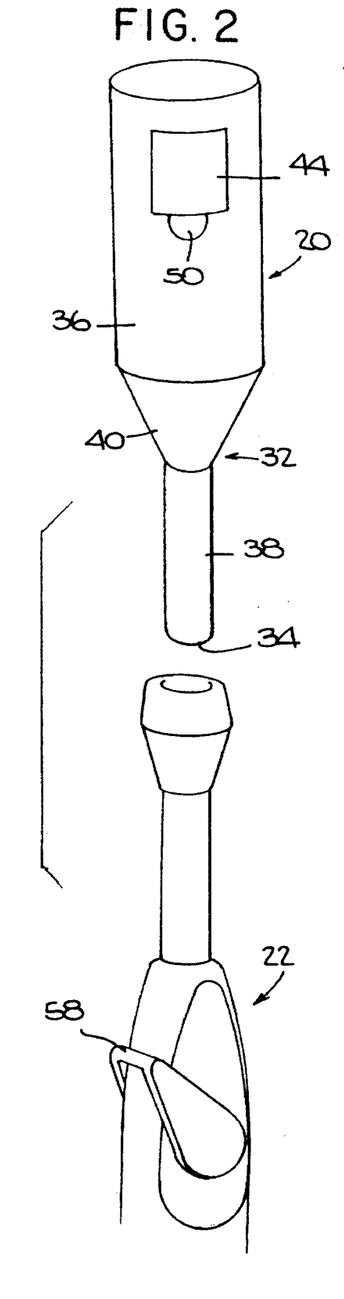
FIG. 2 is an exploded perspective view of a shield according to the invention and a valve assembly for a dental office high volume suction line to which the shield is attached in accordance with the invention.
Figures 3, 4:
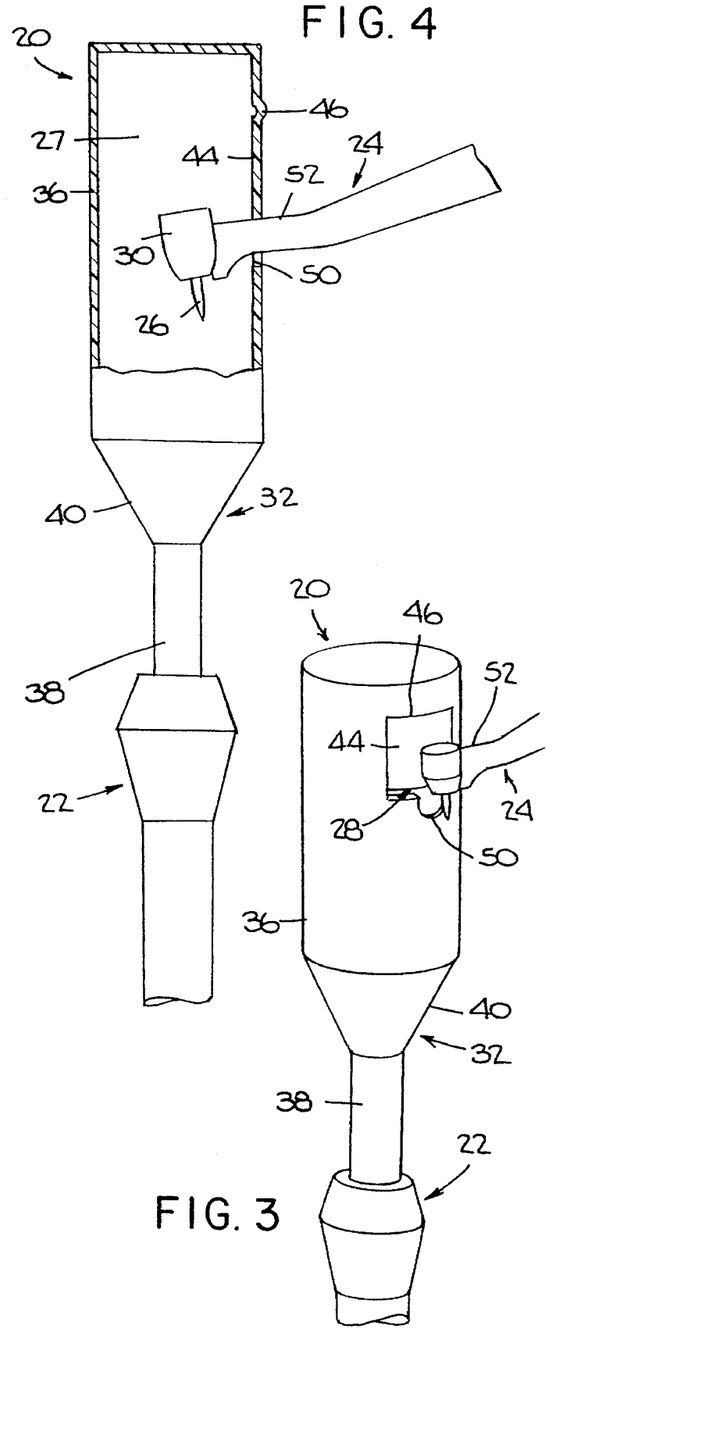
FIG. 3 is a perspective view of the shield depicted in FIG. 2 connected to the high volume suction line valve assembly depicted in FIG. 2 illustrating insertion of the end of a dental handpiece with a burr attached thereto into the shield.
FIG. 4 is a vertical section view partially through the shield depicted in FIG. 2 connected to the high volume suction line valve assembly showing the end of the handpiece within the shield with a door in the shield closed.

Referring to FIGS. 2–4, a shield 20 according to one embodiment of the invention connects to the valve assembly 22 of high volume suction line 16 (shown in FIG. 1) which withdraws the matter ejected from a hand tool 24 shown in FIGS. 3 and 4 during operation thereof. The hand tool 24 may be any dental hand tool such as low and high speed dental handpieces or three way syringes. The hand tool 24 illustrated in the drawings is a high speed hand piece with a rotary tool 26, specifically a burr, connected thereto. The handpiece 24 may be of the disposable or reusable type, and may have a disposable or reusable rotary tool. The shield 20 includes an enclosure 27 (FIG. 4) having a first opening 28 (FIGS. 3 and 5) through which the burr end 30 of handpiece 24 is inserted and removed from the enclosure 27. The shield 20 also has a means for communicating the enclosure with the valve assembly 22, which comprises a section of the shield referenced generally by 32 in communication with the enclosure 27 and terminating in a second opening 34 (FIG. 2) through which the matter ejected from the handpiece is withdrawn into the valve assembly 22 of the high volume suction line 16.

In the embodiment of shield 20 depicted in FIGS. 2–4, the enclosure 27 is defined by a hollow tubular portion 36, and the communicating section 32 of the shield comprises a hollow tubular portion 38 and hollow frustro-conical portion 40 connected at opposite ends fluid-tight to tubular portions 36 and 38. The tubular portion 38 terminates in a circular second opening 34 (FIG. 2), and the frustro-conical portion 38 and the tubular portion 40 communicate enclosure 27 in a fluid-tight manner with the second opening 34. The tubular portion 36 is sized to receive therein the burr end 30 of the handpiece 24, as shown in FIG. 4. The tubular portion 38 is sized to be friction fitted in a substantially fluid-tight manner in the open end of the valve assembly 22 (FIGS. 3 and 4), and the frustro-conical portion 40 acts as a transition between tubular portions 36 and 38. The diameters and lengths of portions 36, 38 and 40 are selected accordingly.

Figure 5:
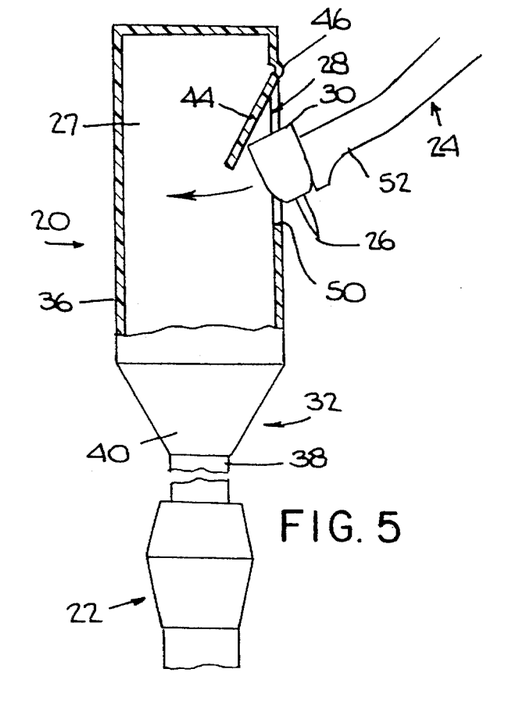
FIGS. 5–8 are section views similar to that of FIG. 4 illustrating the sequence for inserting the end of the handpiece into the shield (FIG. 5), closing the door in the shield with the end of the handpiece within the shield (FIG. 6), operating the handpiece while in the shield (FIG. 7) and removing the end of the handpiece from the shield (FIG. 8)

Referring to FIG. 3, the first opening 28 in the tubular portion 36 of the shield 20 is selectively closed by a door 44. The shield 20 is made of a suitable plastic material and the door 44 is pivotally connected to the first portion 34 by a so-called living hinge 46 (FIG. 4). The door 44 is pivotable into the enclosure 27, as shown in FIGS. 3 and 5, and out of the enclosure, as shown in FIG. 8, to facilitate insertion and removal of the burr end 30 of handpiece 24 into and out of the enclosure 27. The door 44 is sized to frictionally engage the first opening 28 to retain the door in its closed position. This frictional engagement is overcome when the door is pushed opened (FIG. 5) and pulled out (FIG. 8). The first opening 28 preferably has a first portion 28a (FIG. 5) large enough to permit the end 30 of the handpiece to be inserted into and removed from the enclosure 27, and a second portion or extension 50 (FIGS. 2,3 and 5–8) located adjacent the bottom of the first portion 28a sized to receive therein the barrel 52 of the handpiece 24 when the door 44 is closed (FIGS. 4 and 7).

Figure 6:
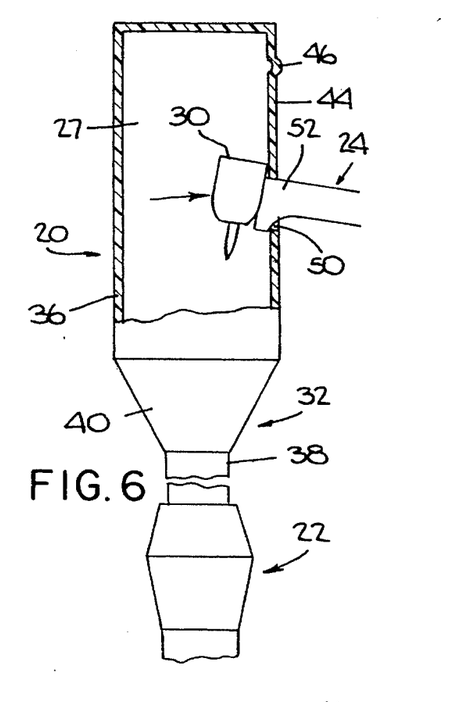
Figure 7:
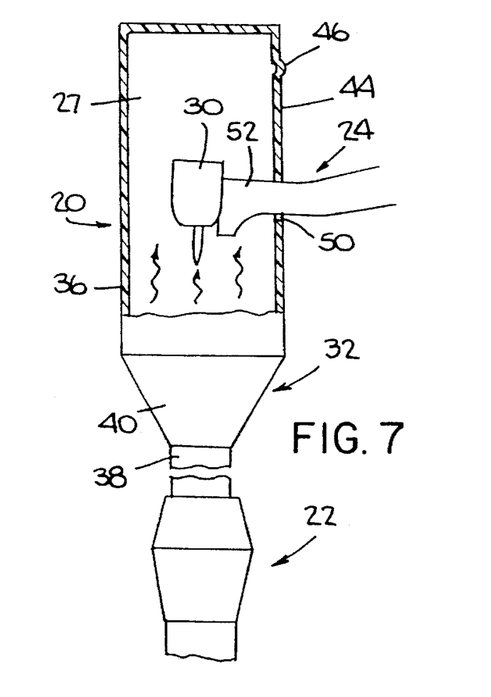
Figure 8:
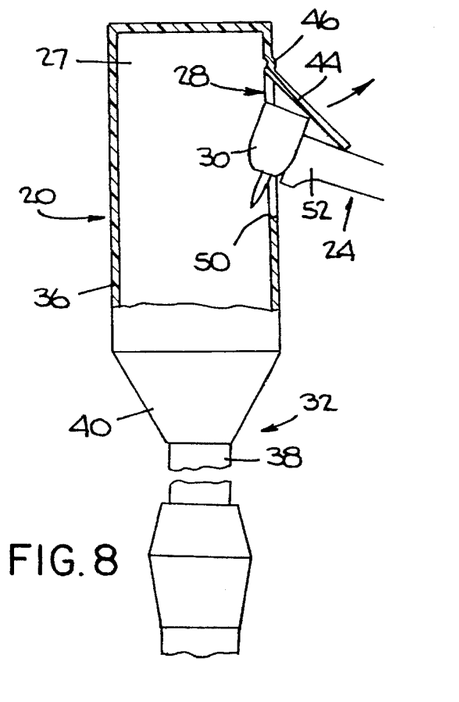

Referring to FIGS. 5–8, the burr end 30 of handpiece 24 may be inserted into enclosure 27, the handpiece operated and then removed from the enclosure using only the hand which holds the handpiece as follows. As shown in FIG. 5, the burr end 30 of the handpiece 24 is used to push the door 44 open into the enclosure 27. Then, the end 30 of the handpiece is moved behind the door 44 and, as shown in FIG. 6, the handpiece barrel 52 is positioned in the extension 50 of opening 28 and the end 30 of the handpiece is used to close the door 44 into frictional engagement with the first opening 28. The end 30 of the handpiece is then positioned within enclosure 27 with the handpiece barrel 52 in extension 50, the lever 58 (FIG. 2) for the valve (not shown) in the valve assembly 22 moved to its open position, and the handpiece is operated as illustrated in FIG. 7. After the handpiece 24 is turned off and the valve lever 58 moved to its off position, the handpiece end 30 is removed from the enclosure 27 by raising the handpiece barrel 52 out of extension 50 and withdrawing the handpiece (FIG. 8) with the end 30 of the handpiece pulling door 44 out of enclosure 27.

The enclosure 27 with the door 44 closed (FIGS. 4 and 7) is completely closed off except for opening 34 into valve assembly 22. As a result, any matter ejected from the handpiece 24 while it is operated within shield 20 is fully contained and is drawn away through the high volume suction line 16. Therefore no mist or solid materials escape the shield 20 (except into the high volume suction line 16), and the risk of contaminating persons in the vicinity of the handpiece while it is operated outside a patient's mouth is essentially eliminated.

The shield 20 is friction fitted to the valve assembly 22 connected to the high volume suction line 16. As a result, whenever the dental professional wants to clean, clear or maintain a hand tool, he or she simply pushes the end (opening 34) of the shield into the valve assembly and follows the procedure described above and illustrated in FIGS. 5–8. Thereafter, the dental professional simply pulls the shield away from the valve assembly 22. Since the shield 20 is preferably made of plastic and can therefore be inexpensive, it can be suitably disposed of after use. However, the shield 20 may also be suitably stored for sterilization and later use. Since the outside of the shield 20 is not substantially contaminated during use, and since the shield need not be touched when inserting and removing a hand tool from the shield, the risk of contamination is further reduced to dental professionals handling the hand tool or shield.

Figures 9, 10, 11:
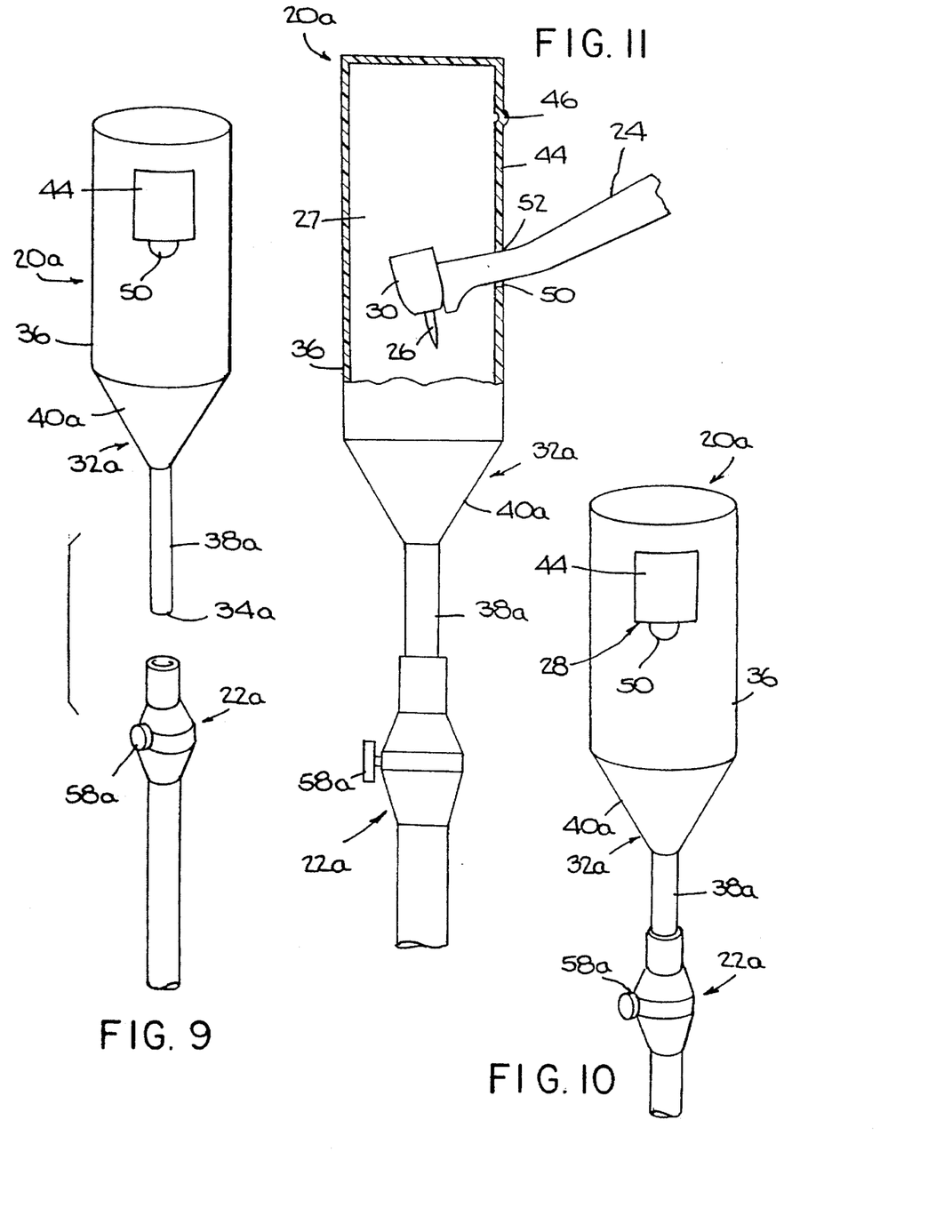
FIG. 9 is an exploded perspective view of a shield according to another embodiment of the invention and a valve assembly for a saliva ejector suction line to which the shield is attached in accordance with the invention.
FIG. 10 is a perspective view of the shield depicted in FIG. 9 connected to the saliva ejector valve assembly depicted in FIG. 9 illustrating insertion of the end of a dental handpiece with a burr attached thereto into the shield.
FIG. 11 is a vertical section view partially through the shield depicted in FIG. 10 connected to the saliva ejector valve assembly showing the end of the handpiece within the shield with a door in the shield closed.

FIGS. 9–11 show a shield 20a for use with a saliva ejector suction line 18 (FIG. 1). Shield 20a is similar to shield 20 in structure, except that tubular portion 38a has a smaller diameter than tubular portion 38 so that it can be friction fitted into a valve assembly 22a (FIG. 9) for the saliva ejector suction line 18. The tubular portion 36 defining the enclosure 27 is essentially the same for shields 20 and 20a, and the frustro-conical portion 40a of shield 20a is structured to connect the tubular portion 36 to the tubular portion 38a. Shield 20a is used in the same way as shield 20.

Figure 12:
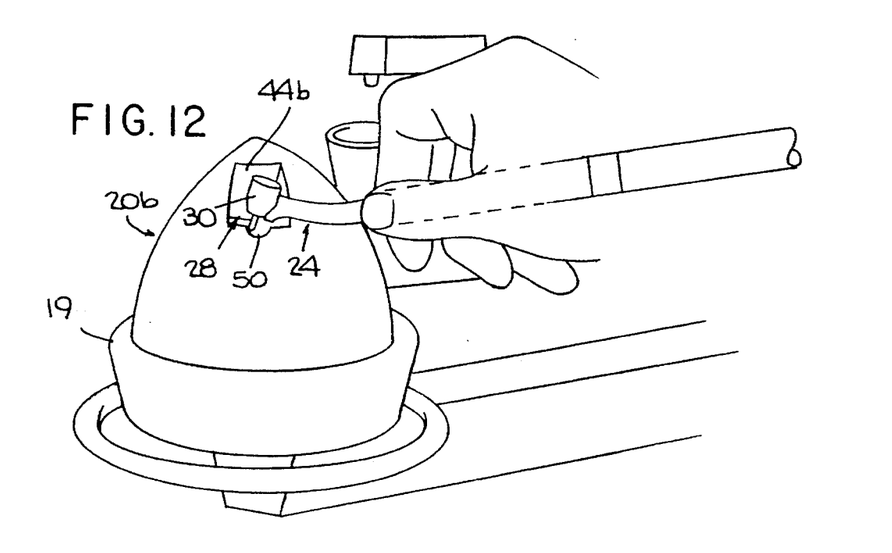
FIG. 12 is an exploded perspective view of a shield according to still another embodiment of the invention and a dental cuspidor which supports the shield in accordance with the invention.
Figure 13:
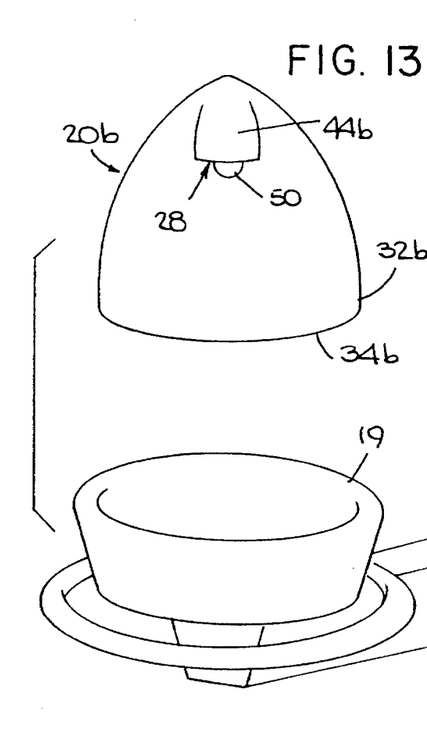
FIG. 13 is a perspective view of the shield depicted in FIG. 12 supported on the cuspidor depicted in FIG. 12 illustrating insertion of the end of a dental handpiece with a burr attached thereto into the shield.
Figure 14:
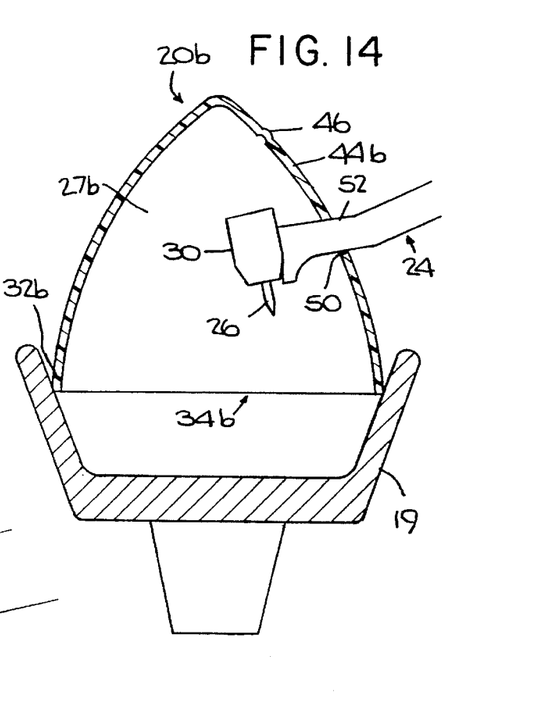
FIG. 14 is a vertical section view through the shield and cuspidor depicted in FIG. 13 showing the end of the handpiece within the shield with a door in the shield closed.

FIGS. 12–14 show a shield 20b for use with a cuspidor 19. In the embodiment of shield 20b depicted in FIGS. 12–14, the enclosure 27b (FIG. 14) is defined by a hollow generally semi-spherical or paraboloidal shape, and terminates in a generally circular opening 34b. The communicating section 32b of the shield 20b simply comprises the periphery of the shield 20b adjacent opening 34b, which is sized to be received in a substantially fluid-tight manner (e.g., loosely friction fitted) within cuspidor 19 as shown in FIGS. 13 and 14. The configuration of enclosure 27b is such to permit the end of a hand tool to be operated therein while the shield is supported in a substantially fluid-tight manner in cuspidor 19.

Referring to FIGS. 12–14, shield 20b includes a door 44b pivotally connected to the shield 20b to selectively close the first opening 28. The door 44b is connected and operated as described above for door 44 and shield 20. The shield 20b is made of a suitable plastic material and may be disposable. The handpiece 24 is inserted into, operated within and removed from shield 20b as described above for shield 20, except that the cuspidor 19 may be operating at all times, or may selectively be turned on and off.

While the invention has been described and illustrated in connection with preferred embodiments, many variations and modifications as will be evident to those skilled in this art may be made without departing from the spirit and scope of the invention. The shapes and configurations of shields 20, 20a and 20b may be different from those illustrated. Also, while the configurations of shields 20, 20a and 20b are adapted for use with the high volume suction line 16, the saliva ejector line 18 and the cuspidor 19, shields according to the invention may have other configurations adapted for use with other waste removal means. The invention as set forth in the appended claims is thus not to be limited to the precise details of construction set forth above as such variations and modifications are intended to be included within the spirit and scope of the invention as defined in the appended claims.

What is claimed is:

1. A shield for use with a dental hand tool, comprising an enclosure of generally hollow semi-spherical or paraboloidal shape sized to receive therein an end of the hand tool from which matter may be ejected during operation of the hand tool, said enclosure having a first opening through which the end of the hand tool may be inserted into and removed from said enclosure, a second opening through which matter ejected from the end of the hand tool may be removed from said enclosure, said second opening being exposed and being circular whereby said enclosure may be supported in a substantially fluid-tight and removable manner in a cuspidor having a circular open end such that any matter ejected from the end of the hand tool is transported away from said shield through said second opening into the cuspidor while substantially preventing escape of the matter ejected from the end of the hand tool except through said second opening into the cuspidor.

2. The shield of claim 1 comprising means for substantially closing said first opening while the end of the hand tool is within said enclosure.

3. The shield of claim 2 wherein said closing means comprises a door and means pivotally connecting said door to said shield adjacent said first opening for pivoting between an open position permitting entry of the end of the hand tool into said enclosure and a closed position substantially closing said first opening while the end of the hand tool is within said enclosure.

4. The shield of claim 3 wherein said door connecting means pivotally connects said door to said enclosure such that said door pivots inwardly into said enclosure into its open position and pivots outwardly to its closed position.

5. The shield of claim 4 wherein said door connecting means pivotally connects said door to said enclosure such that said door pivots outwardly to the outside of said enclosure from its closed position to also selectively open said first opening to permit the end of the hand tool to be removed from said enclosure.

6. The shield of claim 3 wherein said first opening has a first portion closed by said door and a second portion adjacent said first portion sized to receive a barrel of the hand tool therein when said door is closed.

7. The shield of claim 3 wherein said door and said first opening are sized to frictionally engage said door in said first opening to releasably hold said door in its closed position.

8. A shield for use with a dental hand tool, comprising a tubular enclosure sized to receive therein an end of the hand tool from which matter is to be ejected during clearing of the hand tool, said enclosure having a first opening through which the end of the hand tool may be inserted into and removed from said enclosure, and a hollow tubular portion coupled coaxially and fluid-tight to said tubular enclosure with the interior thereof in communication with said enclosure, said tubular portion having a diameter which is less than the diameter of said tubular enclosure, and an open end which is exposed and adapted to be removably received within an end of a tubular suction line with said open end in communication with the interior of the suction line, such that when said shield is coupled to the suction line, escape of the matter ejected from the end of the hand tool is substantially prevented except through said tubular portion and said open end thereof into the suction line.

9. The shield of claim 8 including a frustro-conical portion connecting said tubular enclosure and said tubular portion.

10. The shield of claim 8 wherein said shield comprising closing means having a door and means pivotally connecting said door to said shield adjacent said first opening for pivoting between an open position permitting entry of the end of the hand tool into said enclosure and a closed position substantially closing said first opening while the end of the hand tool is within said enclosure.

11. The shield of claim 10 wherein said door connecting means pivotally connects said door to said enclosure such that said door pivots inwardly into said enclosure into its open position and pivots outwardly to its closed position.

12. The shield of claim 11 wherein said door connecting means pivotally connects said door to said enclosure such that said door pivots outwardly to the outside of said enclosure from its closed position to also selectively open said first opening to permit the end of the hand tool to be removed from said enclosure.

13. The shield of claim 10 wherein said first opening has a first portion closed by said door and a second portion adjacent said first portion sized to receive a barrel of the hand tool therein when said door is closed.

14. The shield of claim 10 comprising means for releasably engaging wherein said door and said first opening are sized to frictionally engage said door in said first opening to releasably hold said door in its closed position.

15. A shield for use with a dental hand tool, comprising a generally hollow semi-spherical or paraboloidal shaped enclosure sized to receive therein an end of the hand tool from which matter is to be ejected during operation of the hand tool, said enclosure having a first opening through which the end of the hand tool may be inserted into and removed from said enclosure, said enclosure having an open end through which matter ejected from the hand tool may exit said enclosure, said end of said enclosure being circular said enclosure being removably supported by a cuspidor having a circular open end with a diameter less than the diameter of said open end of said enclosure with said open end of said enclosure in the open end of the cuspidor and said open end of said enclosure in communication with the interior of the cuspidor in a substantially fluid-tight manner, said enclosure when positioned on the cuspidor substantially preventing escape of the matter ejected from the end of the hand tool except through said open end into the cuspidor.

16. The shield of claim 15 wherein said closing means comprises a door and means pivotally connecting said door to said shield adjacent said first opening for pivoting between an open position permitting entry of the end of the hand tool into said enclosure and a closed position substantially closing said first opening while the end of the hand tool is within said enclosure.

17. The shield of claim 16 wherein said door connecting means pivotally connects said door to said enclosure such that said door pivots inwardly into said enclosure into its open position and pivots outwardly to its closed position.

18. The shield of claim 17 wherein said door connecting means pivotally connects said door to said enclosure such that said door pivots outwardly to the outside of said enclosure from its closed position to also selectively open said first opening to permit the end of the hand tool to be removed from said enclosure.

19. The shield of claim 16 wherein said first opening has a first portion closed by said door and a second portion adjacent said first portion sized to receive a barrel of the hand tool therein when said door is closed.

20. The shield of claim 16 wherein said door and said first opening are sized to frictionally engage said door in said first opening to releasably hold said door in its closed position.

21. The combination of a dental office suction line and a shield for use with dental hand tools, said shield comprising an enclosure sized to receive therein an end of a hand tool from which matter is to be ejected during clearing of the hand tool, said enclosure having a first opening through which the end of the end tool may be inserted into and removed from said enclosure, means for substantially closing said first opening while the end of the hand tool is within said enclosure, and a hollow tubular portion coupled fluid-tight to said enclosure with the interior thereof in communication with said enclosure, said suction line being tubular, said tubular portion having an open end and being adapted to be received within an end of said tubular suction line with said open end in communication with the interior of said suction line, said enclosure when coupled to said suction line substantially preventing escape of the matter ejected from the end of the hand tool except through said tubular portion and said open end thereof into said suction line.

22. The combination of claim 21 wherein said suction line includes a valve assembly which receives said tubular portion of said shield.

23. The combination of claim 22 wherein said suction line is a high volume suction line.

24. The combination of claim 22 wherein said suction line is a saliva ejector line.

25. The combination of a dental office cuspidor and a shield for use with a dental hand tool, said shield comprising a generally hollow semi-spherical or paraboloidal shaped enclosure sized to receive therein an end of the hand tool from which matter is to be ejected during operation of the hand tool, said enclosure having a first opening through which the end of the end tool may be inserted into and removed from said enclosure, means for substantially closing said first opening while the end of the hand tool is within said enclosure, said enclosure having an open end through which matter ejected from the hand tool may exit said enclosure, said cuspidor having an open end having a diameter and said open end of said enclosure having a diameter which is less than the diameter of the open end of said cuspidor such that said enclosure may be removably supported by said cuspidor with said open end of said enclosure in said cuspidor and said open end of said enclosure in communication with the interior of said cuspidor in a substantially fluid-tight manner, said enclosure when positioned on said cuspidor substantially preventing escape of the matter ejected from the end of the hand tool except through said open end into said cuspidor.

* * * * *